United States Patent
Das

(10) Patent No.: US 10,035,023 B2
(45) Date of Patent: Jul. 31, 2018

(54) NETWORK OF INTERNET CONNECTED AUTOMATED EXTERNAL DEFIBRILLATORS

(71) Applicant: Robert Bosch GmbH, Stuttgart (DE)

(72) Inventor: Samarjit Das, Pittsburgh, PA (US)

(73) Assignee: Robert Bosch GmbH, Stuttgart (DE)

(*) Notice: Subject to any disclaimer, the term of this patent is extended or adjusted under 35 U.S.C. 154(b) by 66 days.

(21) Appl. No.: 15/216,907

(22) Filed: Jul. 22, 2016

(65) Prior Publication Data
US 2017/0021185 A1 Jan. 26, 2017

Related U.S. Application Data

(60) Provisional application No. 62/196,219, filed on Jul. 23, 2015.

(51) Int. Cl.
| | | |
|---|---|---|
| *A61N 1/39* | (2006.01) | |
| *H04W 4/90* | (2018.01) | |
| *G08B 25/10* | (2006.01) | |
| *H04W 4/02* | (2018.01) | |
| *H04W 4/22* | (2009.01) | |

(52) U.S. Cl.
CPC ........... *A61N 1/3993* (2013.01); *G08B 25/10* (2013.01); *H04W 4/023* (2013.01); *H04W 4/22* (2013.01); *H04W 4/90* (2018.02)

(58) Field of Classification Search
CPC ...... A61N 1/3993; H04W 4/22; H04W 4/023; G06F 19/327; B01D 2273/30; G08B 25/009; G08B 1/08; G08B 25/00; H04M 1/72536; H04M 3/5116
See application file for complete search history.

(56) References Cited

U.S. PATENT DOCUMENTS

| | | | |
|---|---|---|---|
| 9,026,147 B2 | 5/2015 | Galvin et al. | |
| 9,035,787 B2 | 5/2015 | Bongberg et al. | |
| 9,446,257 B2* | 9/2016 | Baucom | A61N 1/3968 |
| 2008/0122609 A1* | 5/2008 | Mannisto | G08B 19/005 |
| | | | 340/500 |
| 2012/0218102 A1* | 8/2012 | Bivens | G08B 25/003 |
| | | | 340/539.13 |
| 2012/0271370 A1 | 10/2012 | Hochhalter et al. | |

(Continued)

OTHER PUBLICATIONS

International Search Report and Written Opinion corresponding to PCT Application No. PCT/US2016/043665, dated Nov. 2, 2016 (9 pages).

*Primary Examiner* — Mirza Alam
(74) *Attorney, Agent, or Firm* — Maginot Moore & Beck LLP

(57) ABSTRACT

A method of utilizing automatic external defibrillators (AEDs) includes receiving a cardiac emergency alert including a position of the alert at an AED deployment coordinating system connected to an AED network. The deployment coordinating system communicates AED network interface devices and client devices via the AED network and identifies for deployment to the position of the cardiac emergency. The cardiac emergency alert is transmitted to the AED network interface devices associated with the identified AEDs. Information pertaining to the cardiac emergency alert is then displayed on a display of the AED network interface device including the position of the cardiac emergency.

8 Claims, 5 Drawing Sheets

(56) References Cited

U.S. PATENT DOCUMENTS

| | | | | |
|---|---|---|---|---|
| 2013/0053063 A1* | 2/2013 | McSheffrey | .............. | G01S 1/02 |
| | | | | 455/456.1 |
| 2014/0002241 A1* | 1/2014 | Elghazzawi | ........ | H04W 76/007 |
| | | | | 340/8.1 |
| 2015/0112704 A1* | 4/2015 | Braun | .................... | G06Q 10/00 |
| | | | | 705/2 |

* cited by examiner

NETWORK OF INTERNET CONNECTED AUTOMATED EXTERNAL DEFIBRILLATORS

CROSS-REFERENCE TO RELATED APPLICATIONS

This application claims priority to U.S. Provisional Application Ser. No. 62/196,219 entitled "NETWORK OF INTERNET CONNECTED AUTOMATED EXTERNAL DEFIBRILLATORS" by Samarjit Das, filed Jul. 23, 2015, the disclosure of which is hereby incorporated herein by reference in its entirety.

TECHNICAL FIELD

The present invention relates generally to automated external defibrillators, and, in particular, to a method of utilizing automated external defibrillators.

BACKGROUND

Sudden Cardiac Arrest (SCA), also referred to herein as a cardiac emergency, is the onset of an abnormal heart rhythm, lack of pulse and absence of breath, leading to a loss of consciousness. If a pulse is not restored within a few minutes, death occurs. An automated external defibrillator (AED) is a portable electronic device that can be used to automatically diagnose life-threatening cardiac arrhythmias in a patient, and is able to treat them through defibrillation, the application of electrical therapy which stops the arrhythmia, allowing the heart to reestablish an effective rhythm.

The probability of surviving a cardiac emergency often depends on the speed with which an AED can be brought to the scene of a cardiac emergency. To decrease the response time to a patient suffering from a cardiac emergency, portable AEDs are often carried on the person or in the vehicles of emergency and first-response personnel, such as, such as emergency medical technicians (EMTs) and law enforcement officers, firefighters and the like (i.e., "first responders"). In addition, it has become a common practice to place AEDs in public places such as corporate and government offices, shopping centers, airports, airplanes, restaurants, schools and other location where people may congregate (referred to herein as "public access AEDs").

However, first responders cannot be at all places at all times. It still takes time to alert first responders of the occurrence of a cardiac emergency, and first responders may be located a significant distance away from the scene of the cardiac emergency which further increases the response time for providing an AED to the scene. In the case of public access AEDs, it can take additional time for a first responder to retrieve the AED before bringing it to the scene.

What is needed is a system and/or method that enables first responders to be notified quicker of the occurrence and location of a cardiac emergency and that enables and that ensures that first responders and AEDs that can reach the scene of a cardiac emergency the fastest are utilized.

DETAILED DESCRIPTION

Figure 1:
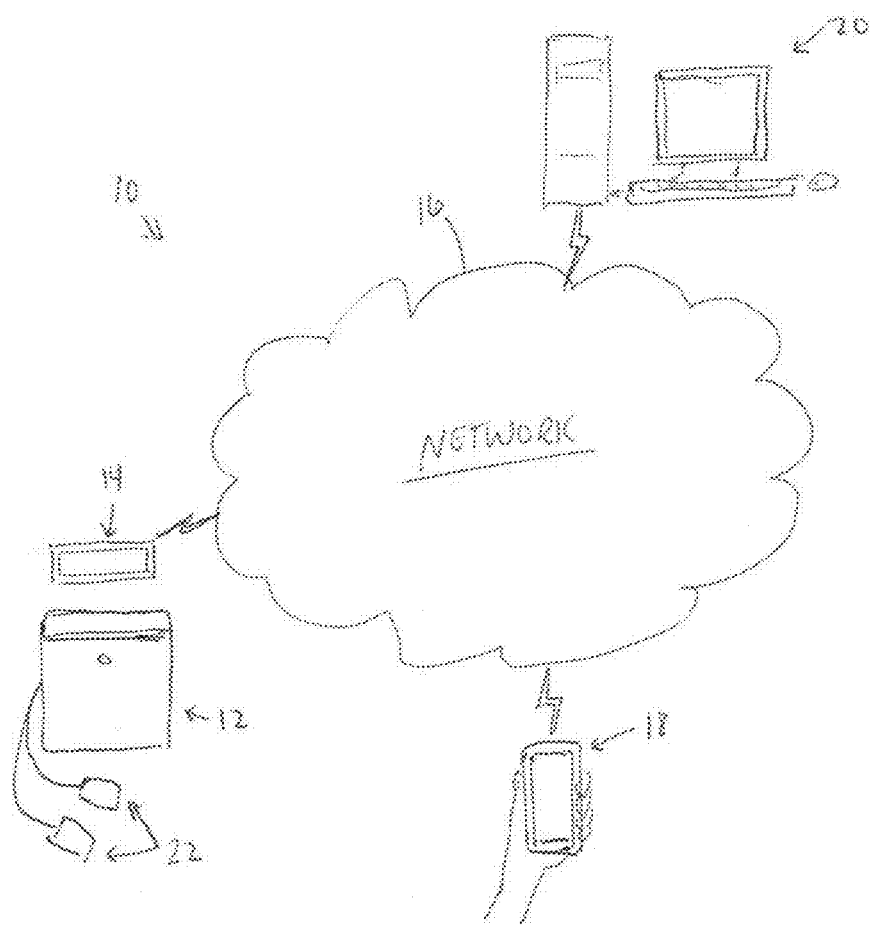
FIG. 1 is a schematic illustration of an AED deployment system according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to a person of ordinary skill in the art to which this disclosure pertains.

The disclosure is directed to a system and method for utilizing automated external defibrillators (AEDs) that connects AEDs, potential first responders and emergency personnel to a network so that the deployment of AEDs to the locations of cardiac emergencies can be crowd sourced to AEDs as well as potential first responders that are nearest to the location of a cardiac emergency. A first responder or emergency personnel at the location of a cardiac emergency can transmit or upload their current position to AED deployment coordinating system connected to the AED network. The AED coordinating system can then identify AEDs that are within a predetermined range of the location of the cardiac emergency and notifies potential responders in the vicinity of the identified AEDs of the location of the cardiac emergency. The system enables AEDs and responders with the potential for the fastest response times to be alerted quickly when a cardiac emergency has occurred. As a result, the response time for an AED to be deployed to the location of a cardiac emergency can be significantly reduced.

FIG. 1 schematically illustrates an AED deployment system 10 in accordance with the present disclosure. As depicted, the AED deployment system 10 includes AEDs 12, AED network interface devices 14, AED network 16, AED client devices 18, and an AED coordinating system 20. AEDs 12 are portable electronic devices that are able to treat cardiac emergency patients through defibrillation. AEDs 12 store electric charge and deliver the electric charge to a patient in the form of an electric current pulse. The electric current is applied to a patient via a set of electrodes 22.

AEDs 12 can comprise public access units which are located in static or fixed positions while not in use. These locations include, but are not limited to, corporate and government offices, shopping centers, airports, airplanes, restaurants, casinos, hotels, sports stadium, schools and universities, community centers, fitness centers, health clubs, theme parks, workplaces and any other location where people may congregate. AEDs are also often carried on the person or in the vehicles of first responders, such as emergency medical technicians (EMTs) and law enforcement officers, firefighters and the like. AEDs 12 which are transported with emergency and first-response personnel are characterized herein as mobile AEDs which can have varying positions.

Referring again to FIG. 1, AEDs are configured to be connected to AED network 16. In general, the AED network 16 may be a cellular network, a telephonic network, an open network, such as the Internet, or a private network, such as an intranet and/or the extranet, or any combination thereof. The network 16 can be any collection of distinct networks operating wholly or partially in conjunction to provide connectivity and may appear as one or more networks to the serviced systems and devices. In one embodiment, communications can be achieved by an open network, such as the Internet, or a private network, such as an intranet and/or the extranet. In one embodiment, communications can be achieved by a secure communications protocol, such as secure sockets layer (SSL), or transport layer security (TLS).

Figure 2:
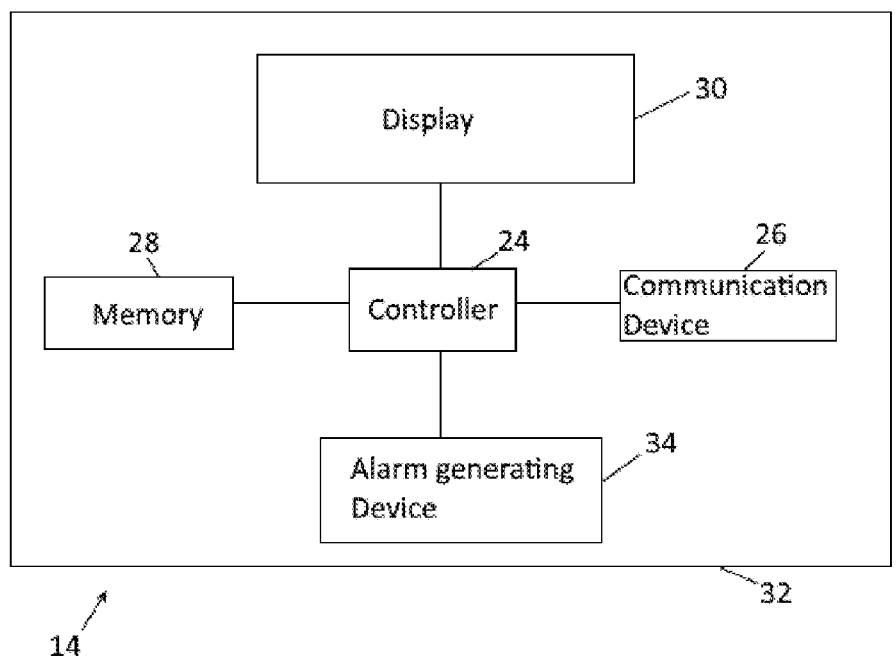
FIG. 2 is a schematic block diagram of an AED and AED network interface device of the AED deployment system of FIG. 1.

To connect to the AED network 16, AEDs 12 are provided with AED network interface devices 14. As depicted in FIG. 2, AED network interface devices 14 may include a controller 24, a communication system 26, a memory 28 and a display 30 which may be provided in a common housing 32. The controller 24 includes a processor (not shown), such as a central processing unit (CPU), an application specific integrated circuit (ASIC), a field programmable gate array (FPGA) device, or a micro-controller. The processor is configured to execute programmed instructions that are stored in the memory 28. The memory 28 can be any suitable type of memory, including solid state memory, magnetic memory, or optical memory, just to name a few, and can be implemented in a single device or distributed across multiple devices. The programmed instructions stored in memory 28 include instructions for implementing the functionality of the system.

The communication system 26 is configured to transmit and receive communication signals via the network 16. The communication system 26 may make use of any suitable type of communication, including wireless and wired communications, radio communications, standard cellular telephone technology, or other two-way communication methods, as well as the appropriate communication protocol, depending on the type of network utilized for the AED network 16, to enable data communications to and from the controller 24.

The controller 24 is configured to operate the display 30 to visually depict information pertaining to the associated AED 12 (FIG. 1). The information depicted on the display 30 may comprise information pertaining to cardiac emergency alerts which may be received via the AED network 16. The cardiac emergency information can include location information which identifies the location of the cardiac emergency. The location information can include the physical address of the emergency, such as the street address, and/or can include global position information, such as global positioning system (GPS) coordinates. The controller 24 may also be connected to one or more alarm generating devices 34, such as lights, buzzers, horns, and the like, which can be activated by the controller to indicate an alarm condition, such as a cardiac emergency.

As depicted in FIG. 1, the AED network interface device 14 can be provided as a separate device from the associated AED 12. As such, the AED network interface device 14 can be mounted onto the AED 12 itself or to a structure, such as a wall or support member proximate the AED. AED network interface devices 14 which are provided separately from the AEDs enable AEDs to be connected to the network 16 without having to modify existing AEDs to include this functionality. Of course, it is also possible for AED network interface devices 14 to be integrated into AEDs 12 during manufacturing so that the network interface devices are integral components of the AEDs rather than separate devices.

Figure 3:
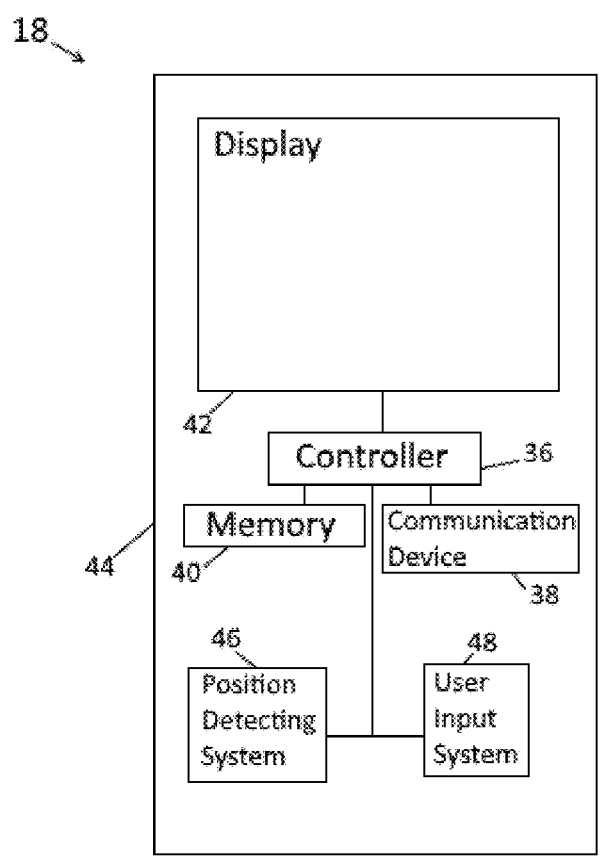
FIG. 3 is a schematic block diagram of a client device of the AED deployment system of FIG. 1.

Client devices 18 are portable devices which can be carried by first responders as well as volunteers and anyone else who is willing to retrieve an AED 12 and transport the AED 12 to the location of a cardiac emergency. Referring to FIG. 3, client devices 18, similar to AED network interface devices 14, include a controller 36, a communication system 38, memory 40 and a display 42 which are provided in a common housing 44. The controller 36 comprises a processor (not shown), such as a central processing unit (CPU), an application specific integrated circuit (ASIC), a field programmable gate array (FPGA) device, or a micro-controller. The processor is configured to execute programmed instructions that are stored in the memory 40. The memory 40 can be any suitable type of memory, including solid state memory, magnetic memory, or optical memory, just to name a few, and can be implemented in a single device or distributed across multiple devices. The programmed instructions stored in memory include instructions for implementing functions of the system.

The communication system 38 is configured to transmit and receive communication signals via the network 16 (FIG. 1). The communication system 16 may make use of any suitable type of communication, including wireless and wired communications, radio communications, standard cellular telephone technology, or other two-way communication methods as well as the appropriate communication protocol, depending on the type of network utilized for the AED network, to enable data communications to and from the controller.

The client device also comprises a position detecting system 46. The position detecting system 46 comprises one or more devices and/or sensors that are configured to detect or determine the current position of the client device 16. Any suitable type of position detection system may be used. For example, position detecting devices may be configured to track position and movements using the Global Positioning System (GPS). The client device 16 may also include a user input system 48, including buttons, a hardware or software implemented keyboard, touch screen, and the like, that enable a user of the device to activate and interact with various functions of the device.

In one embodiment, the client device 16 is embodied as a portable, handheld device, such as a mobile smartphone, tablet, or other type of intelligent mobile device. The technology utilized to connect to and interact with the AED network may be implemented as an application installed on the mobile device and executed by the mobile device's processor. Client devices may also be provided as devices which can be worn or carried on the body of a person, such as a wrist watch, pendant, key chain, clip-on device, and the like (not shown).

Client devices 18 are configured to generate cardiac emergency alerts which are transmitted to the AED deployment coordinating system 20 via the AED network 16. Cardiac emergency alerts can be generated in any suitable manner. In one embodiment, cardiac emergency alerts are generated in response to actuation of a control element of the user input system 48 of the device 16, such as a hardware or software implemented button or switch. The control element may be implemented as part of a special software application, such as a smartphone app, installed on the device. Cardiac emergency alerts comprise position data (as detected by the position detecting system 46) corresponding to the current position of the device 16 which has generated the alert. Other information may also be transmitted along with the cardiac emergency alert if needed or desired, such as patient identification information as well as patient characteristics and mitigating factors that could impact the treatment of the patient.

Client devices 18 are also configured to receive cardiac emergency alerts from the AED deployment coordinating system 20 via the AED network 16. The cardiac emergency alerts received from the AED deployment coordinating system 20 may include position data pertaining to the location of the cardiac emergency as well as location data pertaining to the AED that is to be retrieved if necessary. In response to receiving a cardiac emergency alert, the controller 36 is configured to activate an alarm or notification on the client device 16. For example, the controller 36 may be configured to activate the display 42 to show information indicating the occurrence and location of the cardiac emergency. The controller may also be configured to activate other components of the device to provide a notification of the alert, such as a light, e.g., an LED light, a speaker, or vibration mechanism. Any suitable type of notification and/or alarm may be utilized. The client device 16 may be configured to provide other functionality to facilitate the retrieval and transportation of AEDs 12 to the scene of a cardiac emergency. For example, the client device 16 may include functionality for displaying the location of the AED to retrieve and/or the location of the cardiac emergency on a map as well as navigating to the scene of the emergency.

Figure 4:
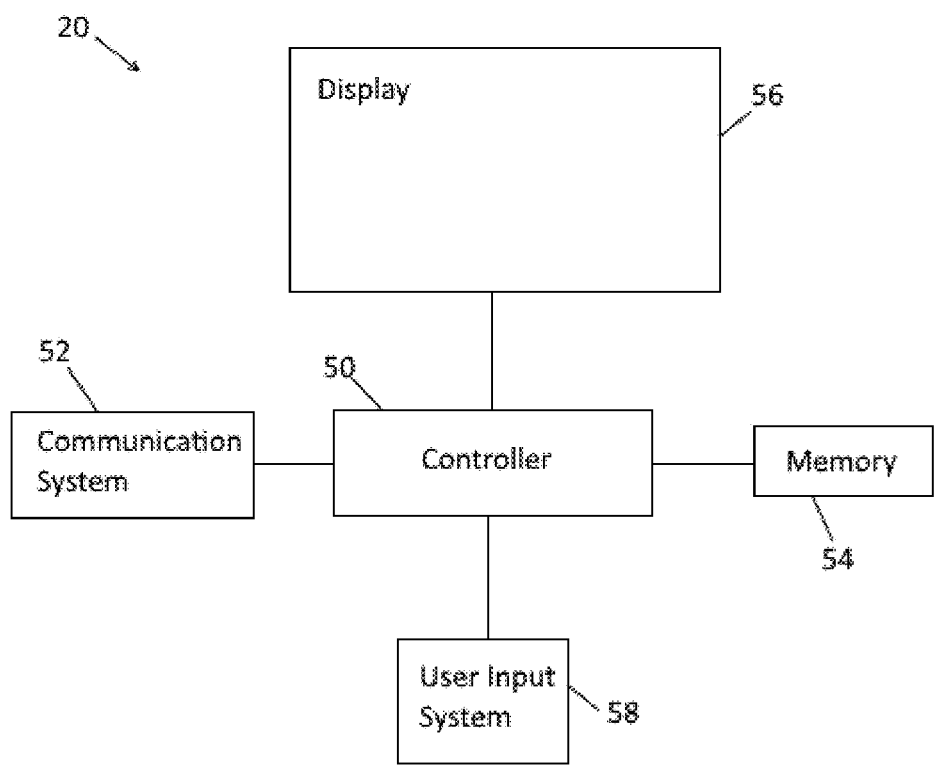
FIG. 4 is a schematic block diagram of an AED deployment coordinating system of the AED deployment system of FIG. 1.

Referring to FIG. 4, AED deployment coordinating system 20 may take the form of a computer or computing system as depicted in FIG. 1. AED deployment coordinating system 20 may comprise a controller 50, a communication system 52, memory 54, a display 56, and a user input system 58. The controller 50 comprises a processor, such as a central processing unit (CPU), an application specific integrated circuit (ASIC), a field programmable gate array (FPGA) device, or a micro-controller. The processor is configured to execute programmed instructions that are stored in the memory 54. The memory 54 can be any suitable type of memory, including solid state memory, magnetic memory, or optical memory, just to name a few, and can be implemented in a single device or distributed across multiple devices.

The communication system 52 is configured to transmit and receive communication signals via the network 16. The communication system 52 may make use of any suitable type of communication, including wireless and wired communications, radio communications, standard cellular telephone technology, or other two-way communication methods as well as the appropriate communication protocol, depending on the type of network utilized for the AED network, to enable data communications to and from the controller.

The programmed instructions stored in memory include instructions for implementing various functions in the system, such as sending data to and receiving data from devices, such as the AED network interface devices 14 and client devices 18, connected to the AED network 16. The data to be transmitted and received via the AED network 16 can include cardiac emergency alerts which indicate the occurrence of a cardiac emergency as well as position data indicating the locations of cardiac emergency alerts and locations of AEDs to be retrieved. The controller 50 is configured to monitor the current positions of devices connected to the AED network 16. This may be accomplished in any suitable manner. For example, the controller 50 may also be configured to maintain a database in memory which includes a list of devices connected to the AED network 16 as well as position data pertaining to each device. Other information pertaining to the devices and the AED network 16 may also be maintained in the database as needed or desired.

The controller 50 is configured to process the data received from the devices connected to the AED network 16 to perform various tasks. For example, the controller 50 is configured to process the position data received from devices 14, 18 connected to the AED network to determine the relative locations of the devices 14, 18 with regard to each other and with regard to the locations of cardiac emergencies. This functionality can be implemented in any suitable manner.

Figure 5:
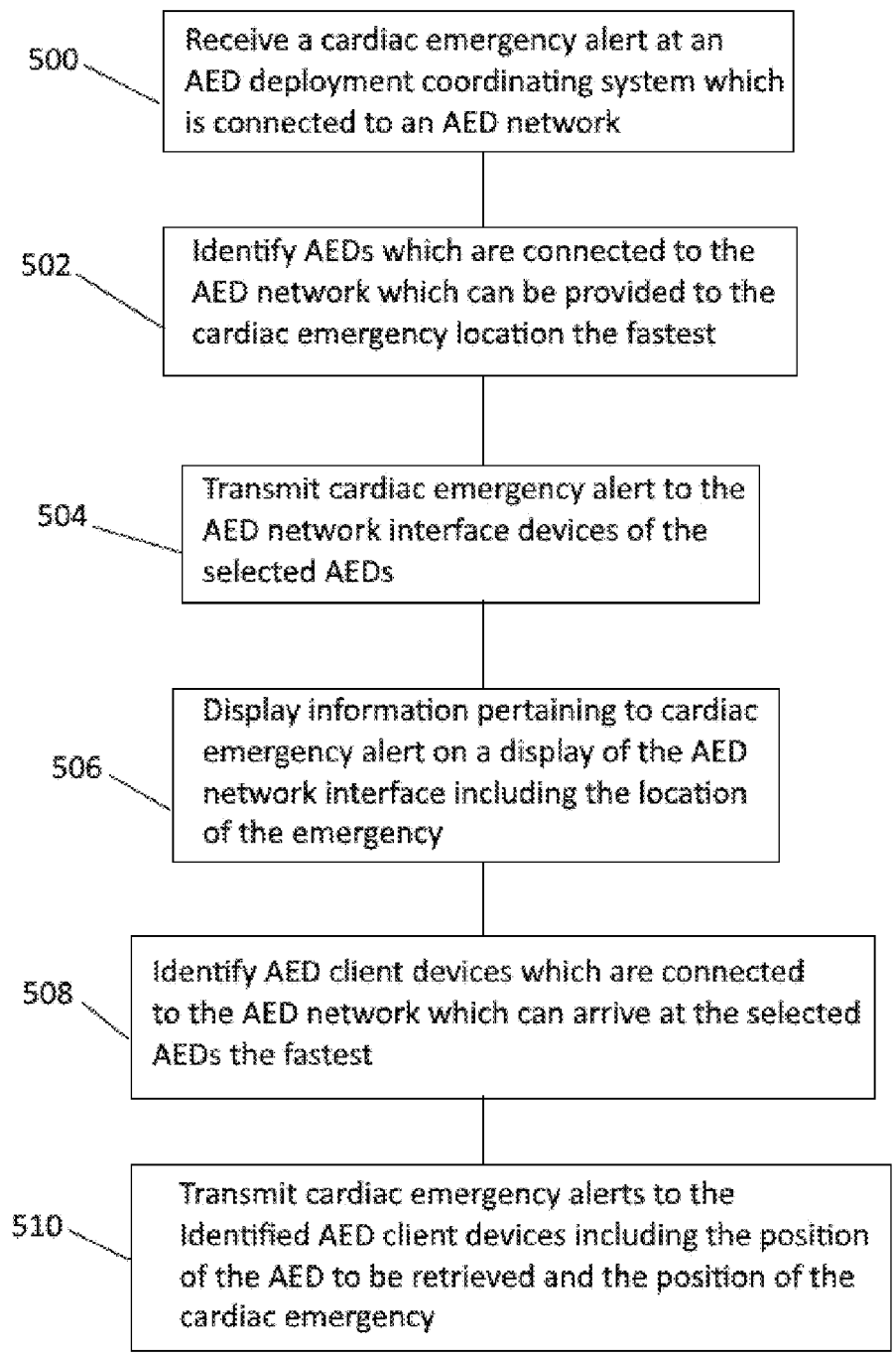
FIG. 5 is a flowchart depicting a method for utilizing the AED deployment system of FIG. 1.

Referring now to FIG. 5, an embodiment of a method implemented by the AED deployment system is depicted. In accordance with the method, the AED deployment coordinating system 20 is configured to receive cardiac emergency alerts (block 500). Cardiac emergency alerts may be transmitted to the AED deployment coordinating system from client devices 18 as described above. Alerts can also be received by means other than the AED network 16. For example, the AED deployment coordinating system 20 may be configured to receive communications from other networks and communication infrastructures (not shown), including emergency communication systems, the internet, telephone systems and the like. To this end, the AED deployment coordinating system 20 may include any appropriate hardware and/or software for communicating with these other systems.

Once the AED deployment coordinating system 20 receives a cardiac emergency alert, the AED deployment coordinating system 20 is configured to identify the AEDs 12 that have the potential to be brought to the scene of the cardiac emergency the fastest (block 502). In other words, the AED deployment coordinating system 20 identifies the AEDs 12 with potentially the fastest response times. These AEDs 12 are then selected to receive the cardiac emergency alert. The cardiac emergency alert, including at least the position data pertaining to the alert, is then transmitted to the AED network interface devices of the selected AEDs via the AED network (block 504).

AED deployment coordinating system 20 can identify the AEDs with the potentially fastest response times in a number of ways. For example, in one embodiment, the AED deployment coordinating system is configured to identify all AEDs within a predetermined range or radius from the location of the cardiac emergency. This can be accomplished in any suitable manner. The predetermined distance for identifying AEDs 12 can be any suitable distance. As examples, the distance may 100 ft, 500 ft, .5 miles, 1 mile, and the like. A distance may be selected arbitrarily or may be selected to produce a desired outcome. For example, a distance may be selected that would result in a predetermined number of AEDs being selected (e.g., 1, 2, 5, 10, or any arbitrary number). Any suitable selection process may be used. A key factor in determining the selection process and how the process is implemented is time. A minimal amount of time should be used in identifying and selecting AEDs 12 in order to minimize the response time.

The AED deployment coordinating system 20 may also be configured to consider travel time associated with client devices 18 and AEDs 12 in identifying and selecting AEDs 12 for deployment. For example, the AED deployment coordinating system 20 may be configured to determine whether AEDs 12 and/or client devices 18 are being carried in vehicles or by pedestrians. AEDs 12 and/or client devices 18 travelling in vehicles may potentially have a faster response time than AEDs 12 and/or client devices 18 which are being carried by a pedestrian travelling on foot. Therefore, the AED deployment coordinating system 20 may be configured to determine an estimated response time for each AED 12 and/or client device 18 based on the mode of travel. Traffic and other factors may also be taken into consideration in determining a response time for an AED or client device. The AED deployment coordinating system 20 may be configured to use the determined response times for AEDs 12 and client devices 18 in making selections for deployment.

Once one or more AEDs 12 have been selected for deployment, the AED deployment coordinating system is configured to transmit the cardiac emergency alert to the AED network interface devices 14 associated with the selected AEDs 12 (block 504). As noted above, the AED network interface devices 14 are configured to display information indicating the occurrence of the cardiac emergency as well as the location of the cardiac emergency (block 506). In addition, any alarm generating devices 34 (FIG. 2), such as lights, buzzers, horns, and the like, associated with the AED network interface device 14 may be activated to indicate that a cardiac emergency is in progress.

The AED deployment coordinating system 20 may also be configured to identify client devices 18 which are capable of reaching the selected AEDs the least amount of time (block 508) and to transmit the cardiac emergency alert to those client devices (block 510) because the persons carrying the alerted client devices 18 will be able to retrieve the selected AEDs the fastest, further reducing the response time for providing the AED to the location of the cardiac emergency. As noted above, the AED deployment coordinating system 20 is configured to monitor the positions of client devices connected to the AED network. Once AEDs 12 have been selected for deployment, the AED coordinating system can then identify client devices 18 that can potentially reach the selected AEDs 12 the quickest.

The selection of client devices 18 to be notified to retrieve AEDs 12 can be implemented in any suitable manner. For example, the selection of client devices 18 to alert can be done in substantially the same manner as the selection of AEDs 12 for deployment, such as by selecting client devices 18 within a predetermined range of the selected AEDs and/or by estimating a response time or travel time for the client devices to the selected AEDs and selecting the client devices having the fastest response times. The AED deployment coordinating system 20 may also be configured to determine whether client devices 18 are located in the same building or same designated area and select these client devices for receiving the alert.

Once one or more client devices 18 have been selected to receive the cardiac emergency alert, the AED deployment coordinating system 20 is configured to transmit the cardiac emergency alert including the position of the AED to retrieve and the position of the cardiac emergency to the selected client devices 18 via the AED network 16 (block 510). As noted above, the controller 56 of the client device may be configured to activate the display to show information indicating the occurrence and location of the cardiac emergency. The controller 56 may also be configured to activate other components of the device to provide a notification of the alert, such as a light, e.g., an LED light, a speaker, or vibration mechanism. Any suitable type of notification and/or alarm may be utilized. The client device 18 may be configured to provide other functionality to facilitate the retrieval and transportation of AEDs to the scene of a cardiac emergency. For example, the client device 18 may include functionality for displaying the location of the AED to retrieve and the locating of the cardiac emergency on a map as well as navigating to the AED and the scene of the emergency.

Once the selected client devices 18 have received the cardiac emergency alert and the person carrying the client device has been notified of the occurrence and location of a cardiac emergency, the person may then attempt to retrieve the AED if required and then deliver the AED to the location of the cardiac emergency. The time needed to notify personal and to retrieve an AED is reduced through the use of the system and method described above which significantly reduces the response times for providing an AED to the scene of a cardiac emergency thereby improving the chances for successfully treating the patient suffering from sudden cardiac arrest.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method of utilizing automatic external defibrillators (AEDs), comprising:
    receiving a cardiac emergency alert at an AED deployment coordinating system, the AED deployment coordinating system being connected to an AED network and being in communication with a plurality of AED network interface devices and a plurality of AED client devices via the AED network, each of the AED network interface devices respectively being associated with a different AED in a plurality of AEDs and being mounted onto the associated AED or mounted to a structure proximate the associated AED, the cardiac emergency alert including a position of the cardiac emergency;
    identifying AEDs of the plurality of AEDs for deployment to the position of the cardiac emergency;
    transmitting the cardiac emergency alert to the AED network interface device associated with each of the identified AEDs, respectively; and
    displaying information pertaining to the cardiac emergency alert, including the position of the cardiac emergency, on a display of each of the AED network interface devices that receives the cardiac emergency alert,
    wherein at least one of the identified AEDs is located within a building, the method further comprising:
    identifying the AED client devices which are located in the building;
    transmitting the cardiac emergency alert to the AED client devices located in the building, the cardiac emergency alert including the position of the cardiac emergency and a position of at least one AED located within the building; and
    displaying cardiac emergency information on the identified AED client devices in response to receiving the cardiac emergency alert, the cardiac emergency information including the position of the cardiac emergency and the position of the at least one AED located within the building.

2. The method of claim 1, further comprising:
    transmitting the cardiac emergency alert to the AED deployment coordinating system from one of the AED client devices.

3. The method of claim 1, wherein identifying the AEDs for deployment to the position of the cardiac emergency comprises:

identifying the AEDs which are within a predetermined distance from the position of the cardiac emergency.

4. The method of claim 1, further comprising:
identifying the AED client devices which are within a predetermined distance from the identified AEDs; and
transmitting the cardiac emergency alert to the AED client devices within the predetermined distance from the identified AEDs, the cardiac emergency alert including the position of the cardiac emergency and a position of at least one AED.

5. The method of claim 1, wherein the AED network comprises an internet.

6. The method of claim 1, wherein at least one of the AED client devices comprises a smartphone.

7. The method of claim 6, wherein the smart phone includes an application that enables the smart phone to connect to the AED network and to interact with the AED deployment coordinating system via the AED network.

8. The method of claim 1, wherein each of the AED client devices include a respective position detecting system for detecting a current position of the corresponding client device, and
wherein each of the AED client devices is configured to transmit the respective current position of the AED client device to the AED deployment coordinating system.

\* \* \* \* \*